(12) United States Patent
Haran et al.

(10) Patent No.: US 8,085,397 B2
(45) Date of Patent: Dec. 27, 2011

(54) FIBER OPTIC SENSOR UTILIZING BROADBAND SOURCES

(75) Inventors: Frank Martin Haran, North Vancouver (CA); Ross MacHattie, Mississauga (CA); Ronald E Beselt, Burnaby (CA)

(73) Assignee: Honeywell ASCa Inc., Mississauga (CA)

( * ) Notice: Subject to any disclaimer, the term of this patent is extended or adjusted under 35 U.S.C. 154(b) by 410 days.

(21) Appl. No.: 12/500,802

(22) Filed: Jul. 10, 2009

(65) Prior Publication Data

US 2011/0007313 A1    Jan. 13, 2011

(51) Int. Cl.
*G01J 3/28* (2006.01)
*G01J 3/10* (2006.01)

(52) U.S. Cl. .......................... 356/328; 356/326

(58) Field of Classification Search .................. 356/326, 356/328
See application file for complete search history.

(56) References Cited

U.S. PATENT DOCUMENTS

| | | | |
|---|---|---|---|
| 4,879,471 A | 11/1989 | Dahlquist | |
| 5,094,535 A | 3/1992 | Dahlquist | |
| 5,166,748 A | 11/1992 | Dahluist | |
| 5,235,192 A | 8/1993 | Chase | |
| 5,773,714 A | 6/1998 | Shead | |
| 5,821,536 A | 10/1998 | Pettit | |
| 6,223,133 B1 | 4/2001 | Brown | |
| 6,570,659 B2 | 5/2003 | Schmitt | |
| 6,775,447 B2 | 8/2004 | Nicholson | |
| 6,784,766 B2 | 8/2004 | Allison | |
| 6,816,243 B2 * | 11/2004 | Shurgalin et al. ............ 356/73.1 |
| 7,116,874 B2 | 10/2006 | Brown | |
| 7,130,512 B2 | 10/2006 | Kuksenkov | |
| 7,288,768 B2 | 10/2007 | Gore | |
| 7,291,856 B2 | 11/2007 | Haran | |
| 7,307,257 B2 | 12/2007 | Long | |
| 7,321,425 B2 | 1/2008 | Haran | |
| 7,411,991 B2 | 8/2008 | Lawrence | |
| 7,446,877 B2 | 11/2008 | Li | |
| 7,494,567 B2 | 2/2009 | Haran | |
| 7,821,633 B2 * | 10/2010 | Jalali et al. .................. 356/301 |
| 2006/0109519 A1 | 5/2006 | Beselt | |
| 2006/0227820 A1 | 10/2006 | Klooster | |
| 2007/0165682 A1 | 7/2007 | He | |
| 2008/0043231 A1 * | 2/2008 | Hasegawa ................. 356/317 |
| 2008/0212091 A1 * | 9/2008 | Tanaka et al. .............. 356/327 |

OTHER PUBLICATIONS

PCT Search Report and Written Opinion for PCT/CA2010/001055 mailed Sep. 7, 2010.
E.A. Mendoza et al, "Miniature Fiber Bragg Gratting Sensor Interrogator System for Use in Aerospace and Automotive Health Monitoring Systems," Proceedings of SPIE. vol. 6758, 87580B, pp. 67580B-10, 2007.

* cited by examiner

*Primary Examiner* — Fannie L. Evans
(74) *Attorney, Agent, or Firm* — Cascio Schmoyer & Zervas

(57) ABSTRACT

Fiber optic sensors employ a high brightness light source such as a fiber optic supercontinuum source, multiplexed superluminescent light emitting diodes, or a broadband tunable laser diode. Light is delivered to the measurement location via fiber optics and sensor optics directs infrared radiation onto material the being monitored that is located in a hostile environment. A disperse element is positioned in the detection beam path in order to separate the wavelengths and to perform spectral analysis. A spectral analysis of the radiation that emerges from the sheet yields information on a plurality of parameters for the material. For papermaking applications, the moisture level, temperature and cellulose content in the paper can be obtained.

23 Claims, 6 Drawing Sheets

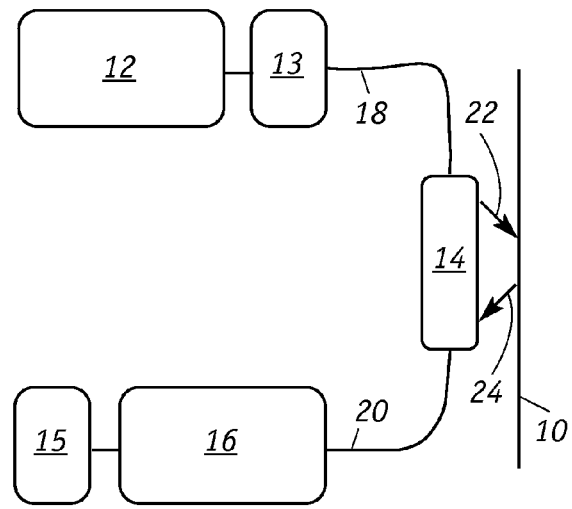
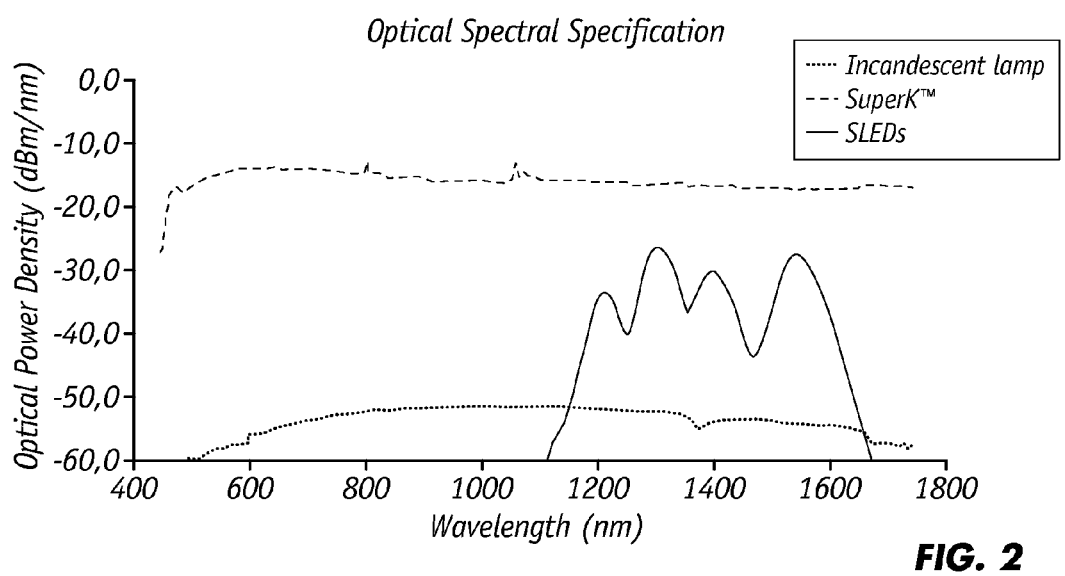
FIG. 1
FIG. 2

FIBER OPTIC SENSOR UTILIZING BROADBAND SOURCES

FIELD OF THE INVENTION

The present invention generally relates to systems for controlling continuous sheetmaking systems and, more specifically, to sensors and methods for simultaneously measuring a plurality of parameters such as the moisture level, temperature and cellulose content in paper and the concentrations of specific polymers in plastics. The technique employs a high brightness light source, such as a fiber optic supercontinuum source, multiplexed superluminescent light emitting diodes (SLEDs), or a broadband tunable laser diode, that is coupled to an optical sensor that scans over the material being monitored.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Many factors influence the rate at which water is removed which ultimately affects the quality of the paper produced.

It is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infrared (IR) region. A monitoring or gauge apparatus for this purpose is commonly employed. Such an apparatus conventionally uses either a fixed gauge or a gauge mounted on a scanning head, which is repetitively scanned transversely across the web at the exit from the dryer section and/or upon entry to the take up reel, as, required by the individual machines. The gauges typically use a broadband infrared source such as a quartz tungsten halogen lamp and one or more detectors with the wavelength of interest being selected by a narrow-band filter, for example, an interference type filter. The gauges used fall into two main types: the transmissive type in which the source and detector are on opposite sides of the web and, in a the case of a scanning gauge, are scanned in synchronism across it, and the scatter type (typically called "reflective" type) in which the source and detector are in a single head on one side of the web, the detector responding to the amount of source radiation scattered from the web. While it is most common to position IR moisture gauges in the more benign dry-end environment, similar gauges are also employed in the hostile wet-end of the papermaking machine. The wet-end moisture gauges are typically located at the end of the press section or the beginning of the dryer section. Gauges in these locations are useful for diagnosis of press and forming sections of the paper machine, or for "setting up" the web for entry into the dryer section.

U.S. Pat. No. 7,291,856 to Haran et al. describes a moisture sensor that uses high brightness superluminescent light emitting diodes (SLEDs) in conjunction with fiber optic delivery to achieve small and compact moisture measurements in hostile and space restricted environments. Specifically, the moisture sensor, which generates non-dispersive spectroscopic measurements of water in paper, is configured so that the sensitive opto-electronic and opto-mechanical components are positioned away from the hostile environment. At the same time, the sensor is capable of delivering a sufficient level of optical power to the measurement location that enables the sensor to maintain measurement speed and repeatability. One drawback of this technique is its limited coarse spectral resolution and limited wavelength range which ultimately restricted its application to measuring moisture. Moreover, in the case of monitoring moisture in paper, the limited spectral diversity of the light source yields data that is grade specific. As a result of this grade dependency, an elaborate calibration procedure is required in order to accommodate papermaking machines that produce a range of weight grades or paper that contains different components, e.g., paper additives.

The industry is in need of a versatile sensor that is capable of measuring a number of different parameters including moisture, temperature and cellulose fiber content early in papermaking processes. Such a sensor will enable better control of the process thereby minimizing off-specification product and minimizing paper breaks.

SUMMARY OF THE INVENTION

The present invention is directed to techniques for simultaneously measuring a plurality of parameters of a material in hostile sheetmaking environments. The invention is based in part on the recognition that a compact optical sensor can be configured to achieve robust coincident measurements by employing a high brightness light source where high spectral intensity light is delivered to and retrieved from the sheet location through optical fibers.

Accordingly, in one aspect, the invention is directed to a sensor system configured to direct illuminating light onto a composition so as to produce detection radiation along a detection beam path for measuring a plurality of parameters in a composition that includes:

a high brightness light source;

means for generating detection radiation from the high brightness light source wherein the detection radiation has predetermined wavelength ranges to detect a plurality of parameters in the composition;

a fiber optic radiation delivery system that delivers the detection radiation to an optical head comprising first optics operable to direct the detection radiation to the composition and second optics operable to direct light that emerges from the composition to a fiber optic radiation retrieval system;

a detector operable to receive and measure light from the second fiber optic radiation delivery system;

a dispersive element that is disposed in the detection beam path; and means for analyzing the light from the fiber optic radiation retrieval system to calculate the plurality of parameters of the composition.

In another aspect, the invention is directed to a method of performing measurements with a sensor that detects a plurality of parameters in a composition that includes the steps of:

providing a high brightness light source that is located remotely from the composition;

providing an optical head comprising a first optics that directs radiation to the composition and a second optics that collects radiation that emerges from the composition;

providing a fiber optic radiation delivery system for directing radiation from the high brightness light source to the first optics;

providing a fiber optic radiation retrieval system for receiving radiation that is directed from the second optics and for transmitting the radiation to a radiation detector, wherein the high brightness light source generates illuminating radiation of sufficient optical power density to produce detection radiation along a detection beam path to the radiation detector;

positioning a dispersive element in the detection beam path; and analyzing the light from the fiber optic radiation retrieval system to calculate the plurality of parameters of the composition.

Preferred high brightness light sources exhibit high spectral bandwidth and these include, for example, fiber optic supercontinuum sources, multiplexed SLEDs, and broadband tunable laser diodes. For measuring properties of paper, the high brightness light source typically generates near infrared radiation. A feature of the invention is that a dispersive element is positioned along the detection beam path in order to separate the wavelengths and to perform spectral analysis. For instance, a tunable bandpass filter, which rapidly tunes through all the source wavelengths onto a single detector, or a diffraction grating, that spatially disperses the source wavelengths onto an array of detectors can be employed. With the dispersive element, a full spectrum of the light that emerges after interacting with the sample, e.g., paper or plastic, is obtained which can be compared to reference spectra. Moreover, from a multivariate calibration analysis of the infrared spectra, the temperature of the water component in the sample, as well as the amounts of water and cellulose present, in the case of paper, can be obtained. Given that the inventive technique yields information for a plurality of parameters of the paper, it is expected that the moisture calibrations derived from the data will be more robust, that is, calibrations can be readily applied to different grades of papers. The same technique can also be applied to measure properties of other multi-component materials such as plastic sheets.

BRIEF DESCRIPTION OF THE DRAWINGS

FIG. 1 is a schematic of a fiber optic sensor system;

FIG. 2 is a graph of optical power density vs. wavelength for different broadband light sources;

DETAILED DESCRIPTION OF PREFERRED EMBODIMENTS

Figure 3:
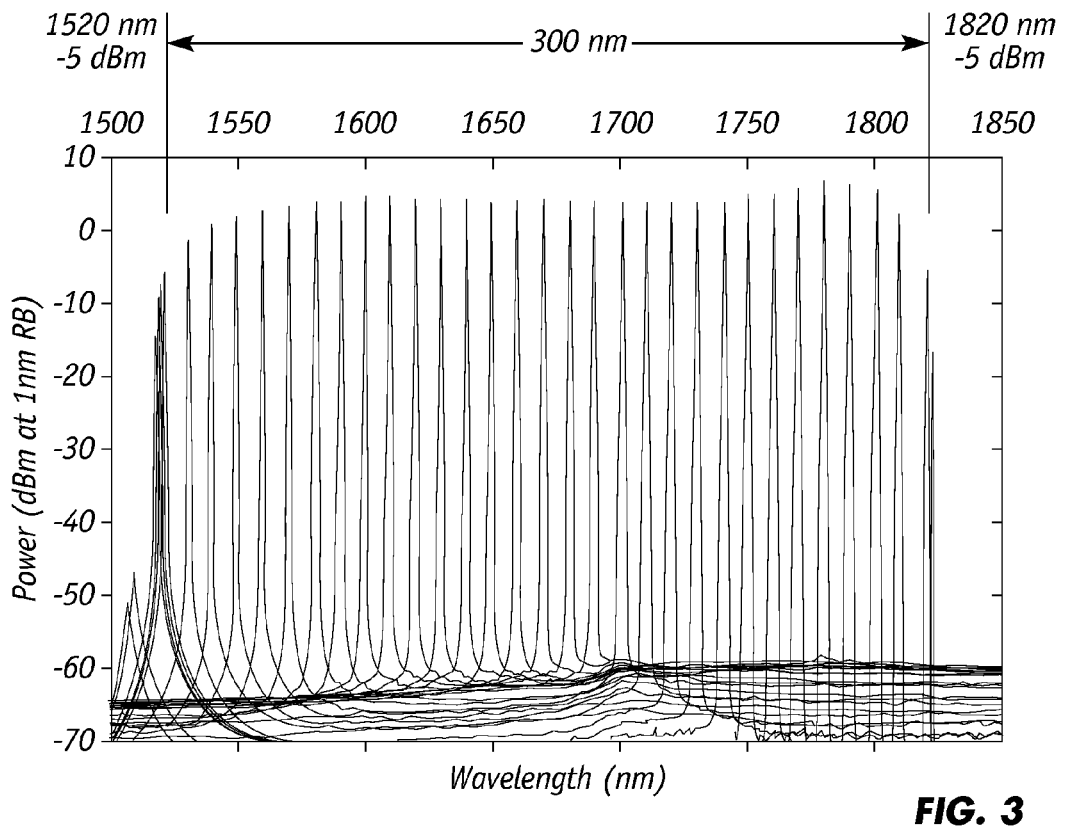
FIG. 3 is a graph of output power vs. wavelength for a tunable light source.

The present invention is directed to a fiber optic sensor system for detecting properties of a composition especially material that is in the form of a film, web or sheet. While the sensor system will be illustrated in measuring properties of paper, it is understood that the sensor system can be employed to measure the presence and content of a variety of spectroscopic measurable components in a number of different materials including, for example, coated materials, plastics, fabrics, and the like.

FIG. 1 illustrates a sensor system of the present invention that is particularly suited for measuring parameters of a sheet of material 10 such as paper. The sensor system includes a high brightness radiation source 12, sensor or optical head 14, a radiation detector 16 and signal processor, e.g., computer, 15. Detection light from high brightness radiation source 12 is delivered to the sensor head 14, which is preferably mobile, through a fiber optic radiation delivery system 18. The sensor head 14 is configured to focus radiation 22 onto sheet 10 and to collect radiation 24 that emerges from, i.e., reflected from or transmitted through, sheet 10. Radiation from sensor head 14 is delivered to radiation detector 16 though a fiber optic radiation retrieval system 20. While dispersive element 13 is shown to be positioned between source 12 and fiber optic delivery system 18, the dispersive element can be positioned anywhere along the detection beam path between high brightness radiation source 12 and radiation detector 16. Electrical signals from radiation detector 16 are communicated to processor 15 where the electrical signals are processed with mathematical models so as to provide useful measurements for a plurality of parameters of sheet 10. High brightness radiation source 12, radiation detector 16, signal processor 15 and their associated components are preferably located remotely from the hostile environment where sensor head 14 operates. Their locations may be a distance of 1 to 100 meters or more from sensor head 14. Suitable high brightness radiation sources have an extremely small emitting area divergence product, i.e., a high brightness, which allows them to be efficiently launched into an optical fiber. Preferred high brightness radiation sources are broadband light sources such as (i) fiber supercontinuum sources or (ii) light-emitting diodes operating at relatively high powers and having a relatively broad spectral width that are known as superluminescent light-emitting diodes (SLEDs) which are available, for instance, from DenseLight Semiconductors Pte. Ltd. (Singapore). Fiber supercontinuum sources are described, for example, in U.S. Pat. No. 7,130,512 to Kuksenkov et al., U.S. Pat. No. 7,116,874 to Brown et al, and U.S. Pat. No. 6,775,447 to Nicholson et al., which are all incorporated herein by reference. Supercontinuum generation is achieved by launching relatively high power light pulses into an optical fiber or microstructure, where the pulse light undergoes significant spectral broadening due to nonlinear interactions in the fiber. The high brightness light source can be a continuous wave (CW) source or a modulated source; the latter could be used to improve signal-to-noise ratio via conventional techniques such as lockin detection.

FIG. 2 exhibits the optical spectral specifications for three different broadband light sources, namely: an incandescent lamp, a white light from a fiber supercontinuum source, which was model SuperK™ from KOHERAS A/S (Birkerød, Denmark), and multiplexed SLEDs. (The optical spectrum from these sources extends beyond a wavelength of 1750 nm but was truncated by the limitations of the spectrometer used to obtain the graph.) In this comparison, the fiber continuum source generates broadband radiation exhibiting very high optical power densities whereas the incandescent lamp generates broadband radiation having insufficient power density for use with the fiber optic sensor system. It should be noted that SLEDs are available, such as those from DenseLight, which exhibit higher spectral power densities than that generated by the SuperK™ that was employed in this example.

Alternatively, the high brightness radiation source comprises a tunable radiation source such, for example, as a micro-electro-mechanical system (MEMS) scanning laser diode source that is available, for instance, from New Focus, Inc. (San Jose, Calif.). FIG. 3 shows the power output in relationship to wavelength over the tuning range of 1520 nm to 1820 nm from an exemplary scanning laser diode source. Regardless of the high brightness source that is used in the fiber optic sensor system, the detection radiation that is generated is selected to include the radiation having the requisite wavelengths for measuring a plurality of parameters in sheet 10 (FIG. 1). In the case of measuring properties of paper, the detection radiation includes near infrared radiation with wavelengths that range from 1 micron to 2.6 microns. As is apparent, not all of thee wavelengths have to be included, that is, sub-ranges within this window can be employed.

Figure 4:
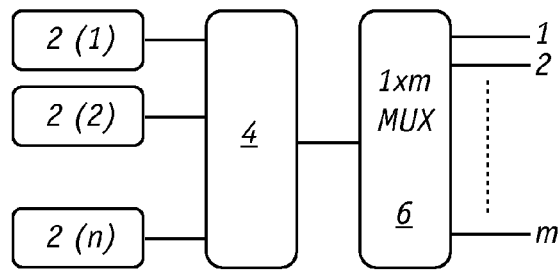
FIG. 4 is a schematic of a broadband radiation source consisting of multiplexed SLEDs.

When SLEDs are employed, detection light from a plurality of SLEDs, each generating radiation at different bandwidths, are preferably managed and transmitted through fiber optic radiation delivery system 18 (FIG. 1) by multiplexing. FIG. 4 illustrates a broadband radiation source arrangement that includes a plurality of SLEDs 2(l) through 2(n) that are coupled by a single-mode optical fiber directional coupler 4 to multiplexer 6 which has corresponding outputs 1 through m that are coupled to individual single-mode optical fibers. Alternatively, the output from the multiplexer can be coupled to a multi-mode optical fiber.

When high brightness light source 12 (FIG. 1) is a broadband light source, radiation detector 16 (FIG. 1) preferably comprises a tunable detector such as (i) a single element photodiode that is equipped with a MEMS tunable bandpass filter or (ii) a detector array. Alternatively, when high brightness light source 12 is a tunable source, radiation detector 16 is preferably a broadband detector such as a single element photodiode.

Figure 5:
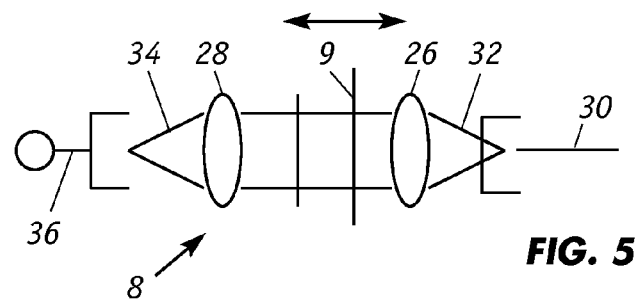
FIG. 5 illustrates a tunable radiation detector with a single element photodiode.

FIG. 5 illustrates a tunable radiation detector 8 that measures light of selected wavelengths from broadband light 32 that is emitted from the distal end of optical fiber 30 of the fiber optic radiation retrieval system 20 (FIG. 1). The tunable radiation detector includes lens 26 that collects and directs light 32 into a tunable bandpass filter 9 such that light 34 of the selected frequency is directed by lens 28 into a single element photodiode 36. Suitable tunable bandpass filters include MEMS tunable bandpass filters. As is apparent, the tunable bandpass filter 9 can be positioned at any suitable location, such as between high brightness light source 12 and sheet 10 (FIG. 1).

Figure 6:
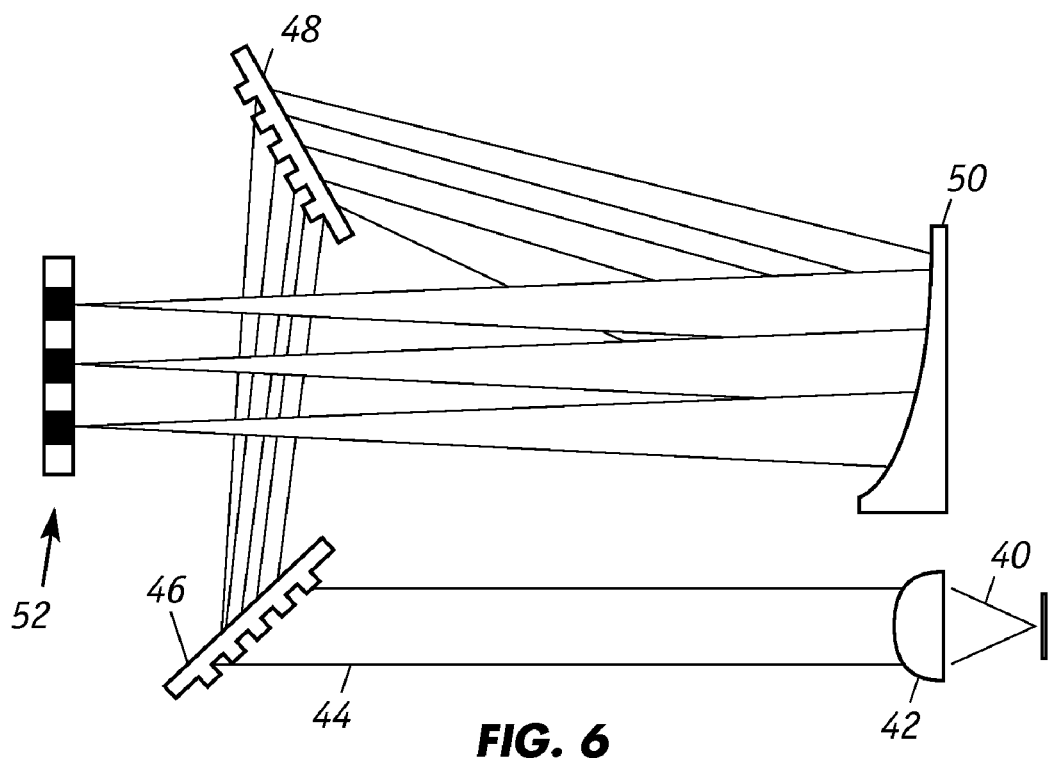
FIG. 6 illustrates a detector consisting of a photodiode array spectrometer.

FIG. 6 illustrates a tunable radiation detector that includes diffraction gratings 46 and 48 and mirror 50. Broadband light 40 that is emitted from the distal end of an optical fiber of the fiber optic radiation retrieval system 20 (FIG. 1) is collimated by lens 42 toward diffraction grating 46. The operation of dispersive components 46, 48 separates the broadband radiation into a frequency spectrum that is measured by an array of photodiodes 52. When a detector array is employed, the dispersive element preferably comprises a linear variable filter or a grating.

When the dispersive element is a tunable filter, it can be positioned anywhere along the detection beam path between high brightness source 12 and radiation detector 16 (FIG. 1). Preferably, the tunable filter is positioned between high brightness source 12 and fiber optic radiation delivery system 18 or between fiber optic radiation delivery system 18 and sheet of material 10 (FIG. 1).

Figure 7:
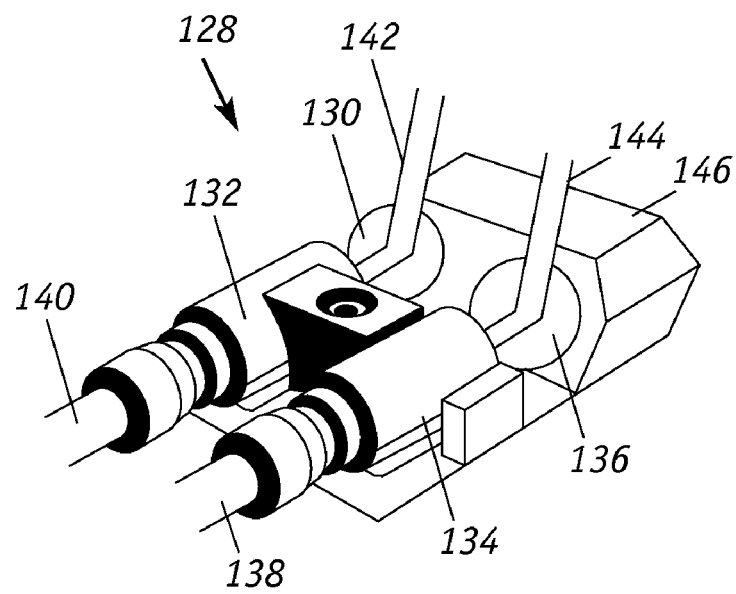
FIG. 7 illustrates an optical head.

FIG. 7 depicts a sensor or optical head 128 that comprises a body 146 with couplers 134 and 132, which incorporate suitable lenses, for connecting optical fiber 138 that delivers detection radiation and optical fiber 140 that delivers reflected radiation, respectively. The optical head may optionally comprise a housing that protects it from the environment. Light 144 that is delivered from optical fiber 138 is reflected from a turning mirror 136 and onto the sheet of material 10 (FIG. 1) that is being scanned. Appropriate lenses, which are incorporated within couplers 132, 134, can be employed. Scattered light 142 from the sheet is reflected from the mirror 130 and into the reflection radiation optical fiber 140. The contours of mirrors 136 and 130 can be fashioned so that light can be imaged onto and then captured from appropriate orientations relative to the moving sheet being scanned; in this case, the focusing lenses (not shown) can be omitted. The mirror's reflective surface can comprise a layer of gold, silver, aluminum, dielectric or other suitable reflective material. The configuration of optical head 128 is for the fiber optic sensor operating in the reflective mode. Dual optical heads as further described are employed when the fiber optic sensor operates in the transmission mode.

Referring to FIG. 1, fiber optic delivery system 18 optically connects stationary high brightness radiation source 12 to mobile sensor head 14. Fiber optic delivery system 18 includes a fiber optic cable containing one or more optical fibers. The optical fibers exhibit the requisite coupling efficiency so that the high optical power output from the high brightness radiation is not significantly attenuation. In addition, the fiber optic delivery system 18 includes a fiber optic cable take-up mechanism that routes the fiber optic cable through a defined path to controls the bending of the cables as mobile sensor head 14 scans back-and-forth over sheet 10. Similarly, fiber optic retrieval system 20 optically connects sensor head 14 to radiation detector 16 and employs a fiber optic cable that is routed through a take-up mechanism. Referring to FIG. 1, fiber optic radiation delivery system 18, which optically connects stationary high brightness radiation source 12 to mobile sensor head 14, includes a fiber optic cable containing one or more optical fibers. The optical fibers exhibit the requisite coupling efficiency so that the high optical power output from the high brightness radiation is not significantly attenuated. In addition, as described herein, fiber optic radiation delivery system 18 includes a fiber optic cable take-up mechanism that routes the fiber optic cable through a defined path to control the bending of the cables as mobile sensor head 14 scans back-and-forth over sheet 10. Likewise, fiber optic radiation retrieval system 20 optically connects sensor head 14 to radiation detector 16 and employs a fiber optic cable containing one or more optical fibers that is routed through a take-up mechanism.

Figure 8A:
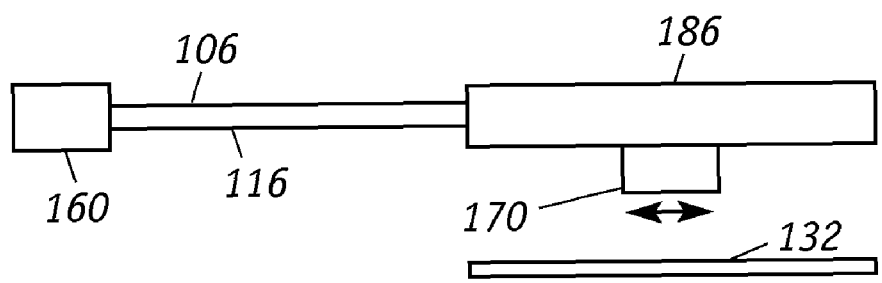
FIGS. 8A and 8B illustrate scanning fiber optic sensor systems operating in the reflection geometry.
Figure 8B:
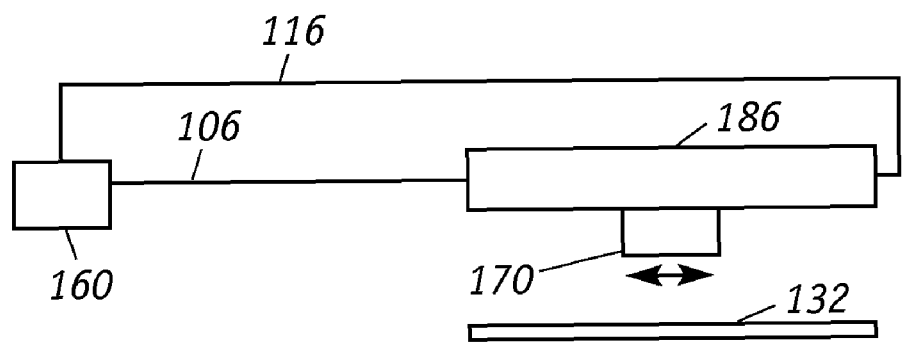

FIGS. 8A and 8B depict the take-mechanism 186 in relationship to the components of the scanning fiber optic sensor operating in the reflection geometry where sensor head 170 is designed to travel back and forth along the cross-direction along the main scanning direction of moving sheet 132 such as paper in a papermaking machine. This width can be one to twelve meters or more. In the embodiment of FIG. 8A, high brightness radiation source 12, radiation detector 16 and signal processor 15 (FIG. 1) are housed in stationary compartment 160, which is located remotely from scanning sensor head 170. Fiber optic cables 106 and 116 can be bundled together in a single cable and routed through take-up mechanism 186 and thus provide optical communication between components within compartment 160 and sensor head 170. Suitable up-take mechanisms are described in US Patent Application 2006/0109519 to Beselt et al., which is incorporated herein by reference. As sensor head 170 moves from one edge of sheet 132 to the other, the take-up mechanism controls the bends in the fiber optic cables.

An advantage to having delivery fiber optic cables 6 and 16 in the same cable structure is that both cables experience the same temperature environment that may be important where there are temperature variations in the scanning sensor system. Alternatively, instead of having the two cables in one structure, the two cables can be deployed side-by-side, in which case, the pulleys of the take-up mechanism will have double grooves as further described herein.

FIG. 8B depicts an alternative embodiment wherein the fiber optic sensor system having a single sensor head 170 is configured for operating in the reflection mode. High brightness radiation source 12, radiation detector 16 and signal processor 15 (FIG. 1) are housed in compartment 160 whereas fiber optic cables 106 and 116 are routed separately through the same take-up mechanism 186 as described further herein. This arrangement is particularly suitable where the fiber optic cables are not exposed to significant temperature variations. Optical communication between components within compartment 160 and sensor head 170 is maintained.

Figure 8C:
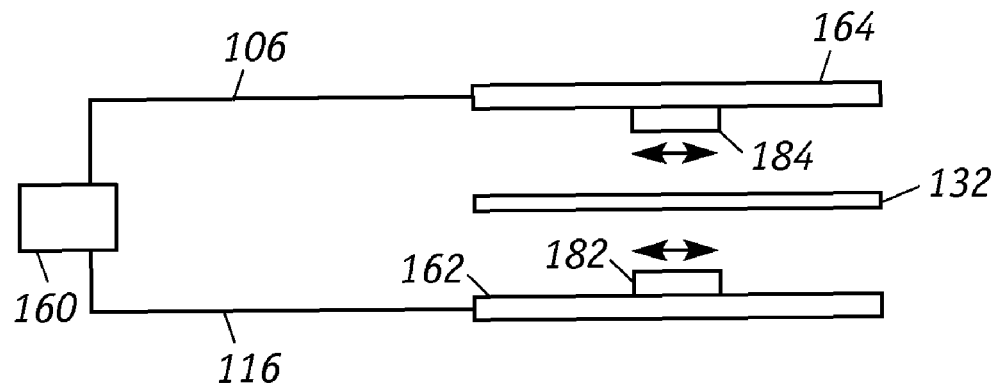
FIG. 8C illustrates a scanning fiber optic sensor system operating in the transmission geometry.

When operating in the transmission mode, the fiber optic sensor system has dual sensor heads that are positioned on opposite sides of material being monitored. One sensor head is in communication with the high brightness light source and serves to direct detector radiation onto the material whereas the second sensor head is in communication with the detector and serves to receive radiation that is transmitted from the material. FIG. 8C depicts the take-up mechanisms 162, 164 in relationship to the components of the scanning fiber optic sensor system operating in the transmission geometry where dual sensor heads 182, 184 are designed to travel back and forth along the cross-direction along the main scanning direction of moving sheet 132. High brightness radiation source 12, radiation detector 16 and signal processor 15 (FIG. 1) are housed in stationary compartment 160. As sensor head 182 moves from one edge of sheet 132 to the other, the take-up mechanism controls the bends in the fiber optic cable. Similarly, for sensor head 182, which is also designed to move along the cross-direction of moving sheet 132, sensor head 182 is in optical communication with fiber optic cable 116, which is routed through take-up mechanism 162.

In operation, the movements of the dual scanner heads 182, 184 are synchronized with respect to speed and direction so that they are aligned with each other. Scanning systems having sensor components on opposite sides of the sheet being analyzed are described, for example, in U.S. Pat. No. 5,773,714 to Shead and U.S. Pat. No. 5,166,748 to Dahlquist, which are incorporated herein by reference.

Figure 9A:
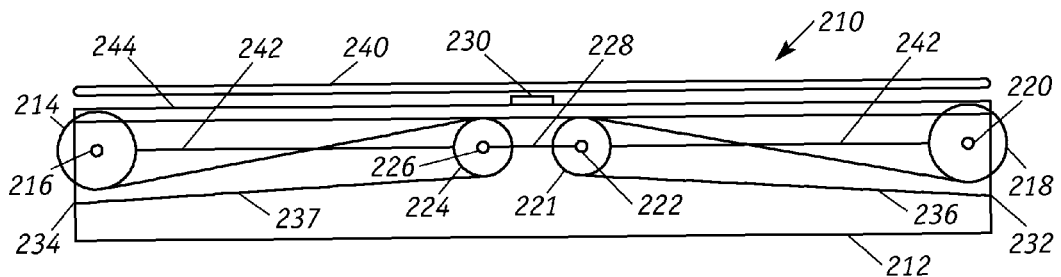
FIGS. 9A and 9B are side schematic views of a fiber optic cable take-up mechanism.
Figure 9B:
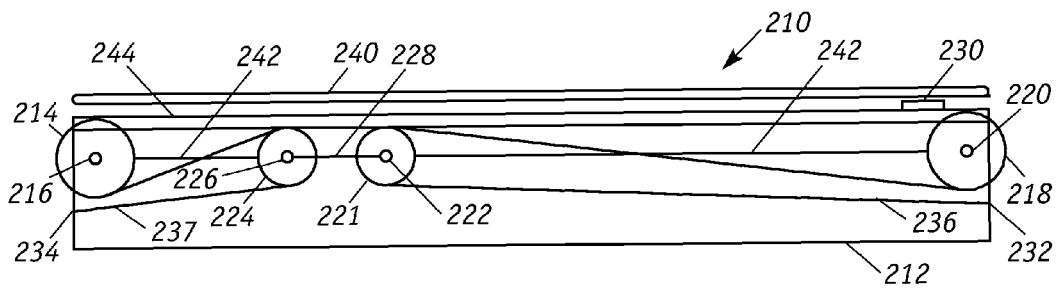

FIGS. 9A and 9B illustrate an embodiment of a cable take-up mechanism 210 that facilitates the movement of scanner head 230 along the cross direction of a moving sheet or web 240. Located on one side of frame 212 is a first fixed turning pulley 214, which is secured to the frame by pin 216. Positioned on the other side of the frame is second fixed turning pulley 218, which is secured by pin 220. The distance between pins 216 and 220 preferably ranges from one to twelve meters. The diameters of the two fixed turning pulleys 214, 218 are preferably the same. Each pulley preferably has a groove around its outer perimeter that is dimensioned to accommodate a flexible cable.

Situated within frame 212 and positioned between the two fixed pulleys 214, 218 are a pair of movable or translating pulleys 221, 224 that are linked to each other by a rigid member 228. The pair of movable pulleys 221, 224 is secured by pins 222 and 226, respectively, to a rail 242 which allows the movable pulleys 221, 224 to move back-and-forth along a linear path between the fixed turning pulleys 214, 218. Preferably, the diameters of the movable pulleys 221 and 224 are the same but they are preferably smaller than the diameters of the fixed turning pulleys 214, 218. The centers of the four pulleys 214, 218, 221 and 224 are preferably aligned along a horizontal axis.

In the case where the fiber optic sensor system is operating in the reflection mode so that only a single take-up mechanism is required, a fiber optic cable 236, representing fiber optic cable 106 (FIG. 8A), is partially wound around pulleys 221 and 218. Cable 236 terminates at sensor head 230 while the cable at position 232 is secured to frame 212 or other stationary structure. Another fiber optic cable 237, representing fiber optic cable 116 (FIG. 8A), is partially wound around pulleys 224 and 214. Cable 237 also terminates at sensor head 230 while the cable at position 234 is secured to frame 212 or other stationary structure. Both cables 236 and 237 should be secured with sufficient tension to avoid excessive slack. No spring or other tension device is needed to secure the two ends.

The scanner head 230 is operatively connected to the cables 236 and 237 as it scans back and forth along the cross direction between the sides of the moving sheet 240. The linked translating pulleys 221, 224 move in the opposite direction to that of scanner head 230 but travels at half the speed. In this fashion, cables 236 and 237 remain taut throughout from one end 232 to the other end 234 even when scanner head 230 is in motion. In another embodiment, it is recognized that as the take-up mechanism operates over time, a certain amount of creep may develop in the cable. Thus, the take-up mechanism can be equipped with a spring or other tension device at one or both ends 232 and 234. This will prevent the cable from exhibiting excessive slack. Alternatively, the spring can be positioned in another part of the take-up mechanism such as between the pair of movable pulleys 221, 224. In this case, instead of being connected by a rigid member 228, a member with a spring device can be employed to connect the two of movable pulleys 221, 224.

As is apparent, in the cable take-up mechanism as shown in FIGS. 9A and 9B, the optical fiber cables are guided around a series of pulleys that determine the bend diameters of each optical fiber cable. The cables are maneuvered through a defined route. The set of translating pulleys 221, 224 allows the cables to stay under tension without the need of a spring or a loading device. The translating pulleys, which move in unison, assure that the tension on the cables is maintained essentially constant throughout each cable's length. Movement of the translating pulleys in a direction that is opposite to that of scanning head 230 serves to distribute each cable in the direction where it is needed in response to the forces that move the scanner head 230. As illustrated in FIGS. 9A and 9B, as the scanner head 230 moves from one side toward the middle of the cable take-up mechanism 210, reduction in the length of one cable between fixed turning pulley 214 and translating pulley 224 is offset or compensated by a corresponding increase in tile length of the other cable between fixed turning pulley 218 and translating pulley 221.

Figure 10:
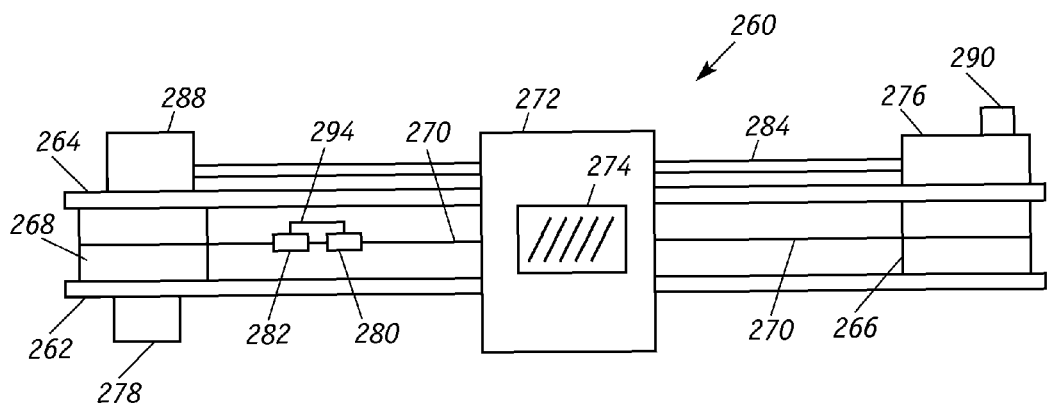
FIG. 10 is a top plan schematic view of a fiber optic cable take-up mechanism.

The scanner head 230 can be advanced back and forth along the cross direction by a number of mechanisms. In one embodiment, as illustrated in FIG. 10, the cable take-up mechanism 260 includes rails 262 and 264, fixed turning pulleys 266 and 268, and a pair of moving pulleys 280 and 282, which are linked by a rod 294. A carriage 272 rest on top of the rails 262, 264, which function as low-friction guides for the carriage 272 as it travels back and forth. The carriage 272, which can be a platform with rollers, supports scanner head 274. In this arrangement, the scanner head 274 is positioned underneath a web to be analyzed, however, it is understood that the cable take-up mechanism 260 can be employed so that the scanner head 274 is directly above or, at angle relative to, the web to measure properties from its top surface.

In the reflection mode, scanner head 274 can have the configuration shown in FIG. 7. Thus, detector signals are transmitted from scanner head 274 through cable 270 to compartment 278. Carriage 272 is connected to a belt 284 that is wound around drive pulley 276 and driven pulley 288, which is operatively connected to motor 290. In operation, control of motor 290 regulates the speed and direction of the movement of the carriage 272. Alternatively, belt 284 can be secured directly to the rod 294, which links the pair of movable pulleys 280, 282. In this fashion, activation of motor 290 also moves cable 270. As another alternative, motor 290 can be operatively connected to fixed turning pulley 266 to drive scanner head 274.

In the case where the fiber optic scanning sensor is operating in the transmission mode as illustrated in FIG. 8C with separate take-up mechanisms on each side of the product being measured, cable take-mechanism 210 as illustrated in FIGS. 9A and 9B essentially operates the same way as described previously except that only one of cable 236 or 237 is a delivery fiber optic cable 106 or 116 (FIG. 8C). The other cable can comprise a non-active cable to maintain symmetry.

In the case where the fiber optic scanning sensor is operating in the reflection mode as illustrated in FIG. 8A with a single take-up mechanism, cable take-mechanism 210 as illustrated in FIGS. 9A and 9B one of cable 236 or 237 consists of a single cable structure that includes both delivery fiber optic cables 106 and 116 (FIG. 8C). In this fashion, the two fiber optic cables are routed through the take-up mechanism along coextensive paths. The other cable can comprise a non-active cable to maintain symmetry. Alternatively, if the two delivery fiber optic cables are deployed separately but side-by-side, then the pulleys in take-up mechanism have dual grooves to accommodate them. The pair of non-active cables can be deployed side-by-side to maintain symmetry.

With the cable take-up mechanism, the total bend loss as the optical head moves back-and-forth during scanning is essentially preserved. This is important for scanners that use a spectroscopic sensor that measures the relative powers in two or more different wavelength bands. Bend loss in an optical fiber depends upon bend radius and total bend length. If the bend length or the bend radius changes as the mobile optical head is scanned, measurement errors will be introduced. The cable take-up mechanism keeps the angular bend length and the bend radius constant even as the optical head is moving; this in turn minimizes any sensor error. (Note however that the bend positions are changing.) The bend length for the optical fiber is analogous to the length of an arc, which is a segment of a circle. The bend length for an arc is equal to the product of the diameter and the angle between two radii as measured in degrees radian. Thus, an arc that spans 90 degrees has twice the bend length as an arc with the same radius that spans only 45 degrees. The cable take-up mechanism essentially maintains the same total bend length during scanning. Controlling the bend length and tension between the two delivery optical fiber cables 106 and 116 helps preserve the optical path difference between the power source and the detector optical fiber cables.

Figure 11:
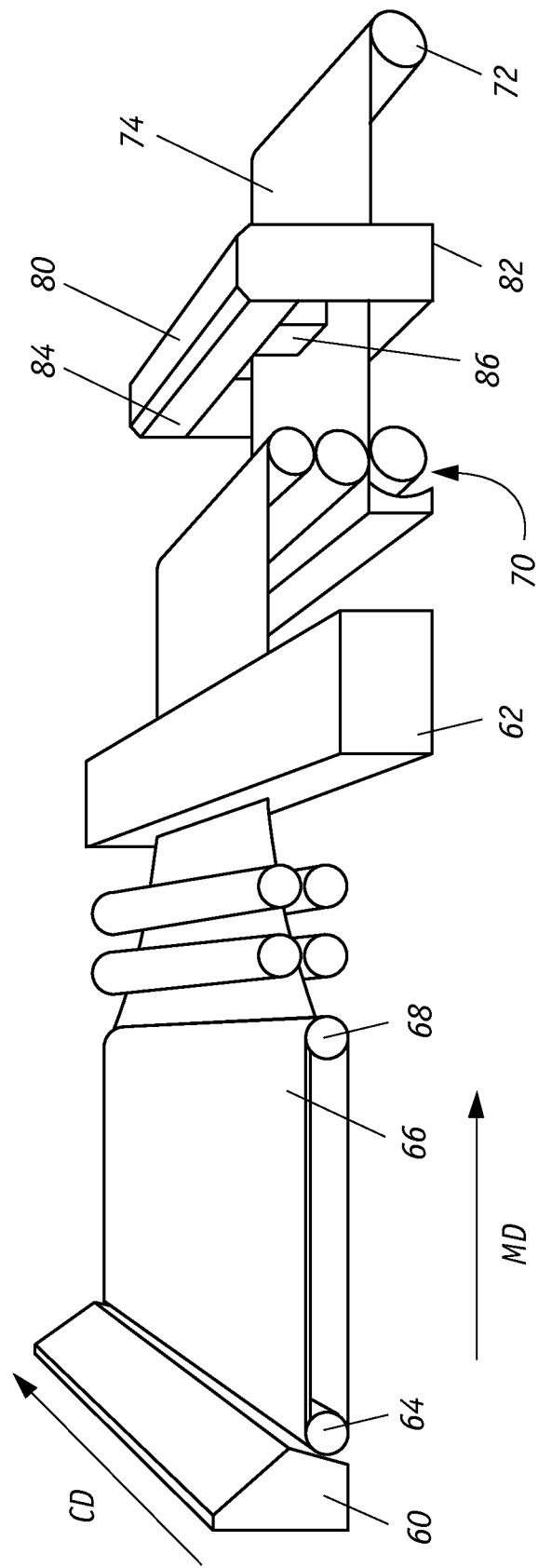
FIG. 11 illustrates a sheetmaking system incorporating the fiber optic sensor system.

The fiber optic sensor can be used to measure physical characteristics of an aqueous mixture in a sheetmaking system and is particularly suited for obtaining wet-end coincident cellulose, temperature and moisture measurements. The fiber optic sensor is illustrated herein as part of a scanning system however it is understood that the fiber optic sensor can be employed at multiple fixed point locations using standard multiplexing techniques. FIG. 11 shows a typical sheetmaking system for producing a continuous sheet of paper material 74 including a headbox 60, a steambox 62, a calendaring stack 70, a take-up reel 72 and scanner system 80 that includes the inventive fiber optic sensor system. In headbox 60, actuators are arranged to control discharge of wetstock onto supporting wire or web 66 along the cross direction (CD). The sheet of fibrous material that forms on top of wire 66 is trained to travel in the machine direction (MD) between rollers 64 and 68 and passes through a calendaring stack 70, which includes actuators that control the compressive pressure applied across the paper web. The sheetmaking system includes a press section preceding steambox 62 where water is mechanically removed from the sheet and where the web is consolidated. Thereafter, water is removed by evaporation in the dryer section. The finished sheet product 74 is collected on a reel 72.

The scanner system 80 generally includes pairs of horizontally extending guide tracks 84 that span the width of the paper product 74. The guide tracks are supported at their opposite ends by upstanding stanchions 82 and are spaced apart vertically by a distance sufficient to allow clearance for paper product 74 to travel between the tracks. The sensor is secured to a carriage 86 that moves back-and-forth over to paper product 74 as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein fully by reference.

With the fiber optic sensor system, it is expected that measurements can be made early in the papermaking process immediately after the paper exits the forming section from wire 66. Moreover, by utilizing broadband sources, the sensor is able to achieve a full spectral analysis while still maintaining measurement speed and repeatability in a hostile space, restricted environments. It is expected that the measurements, which include a plurality of parameters of the product being monitored, will be more robust. In the case of paper, besides moisture content, the amount of cellulose present as well as the sheet temperature can be ascertained. These additional measurements are made possible by the increased spectral resolution and range of the sensor to generate fast, accurate high resolution near infrared spectra. With the presence of these additional measurements in a small, robust sensor, it is possible to control temperature and fiber (cellulose) weight parameters further up the papermaking machine for a tighter control loop.

Desired properties of the paper are determined by standard chemometric techniques. For example, multivariate models are used to relate multivariate analytical measurements such as infrared spectra (independent variables) to component concentrations and physical properties (dependent variables). In calibrating these models, data (spectra and concentrations/properties) are measured for a set of calibration samples and a regression model is developed to relate the dependent variable to the independent variables. Multivariate mathematical techniques are typically performed in general purpose computers suitable for running commercially available software programs. Numerous software packages are currently available. Examples of the available software packages include, but are not limited to "AnaGrams," available from Orbital Sciences of Pomona, Calif.; MATLAB® available from The Math Works, Inc., of Natick, Mass.; Pirouette®, available from Infometrix, Inc., of Woodinville, Wash.; and Spectral ID®, available from Thermo Galactic, of Salem, N.H.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

The invention claimed is:

1. A sensor system configured to direct illuminating light onto a composition so as: to produce detection radiation along a detection beam path for measuring a plurality of parameters in a composition that comprises:
   a high brightness light source;
   means for generating detection radiation from the high brightness light source wherein the detection radiation has predetermined wavelength ranges to detect a plurality of parameters in the composition;
   a fiber optic radiation delivery system that delivers the detection radiation to an optical head comprising first optics operable to direct the detection radiation to the composition and second optics operable to direct light that emerges from the composition to a fiber optic radiation retrieval system;
   a detector operable to receive and measure light from the fiber optic radiation retrieval system;
   a dispersive element that is disposed in the detection beam path; and
   means for analyzing the light from the fiber optic radiation retrieval system to calculate the plurality of parameters of the composition.

2. The sensor system of claim 1 wherein the high brightness light source comprises a fiber supercontinuum source.

3. The sensor system of claim 2 wherein the dispersive element comprises a tunable bandpass filter or a grating spectrometer.

4. The sensor system of claim 2 wherein the detector comprises a detector array and the dispersive element comprises a grating spectrometer or a linear variable filter.

5. The sensor system of claim 1 wherein the high brightness light source comprises a plurality of superluminescent light-emitting diodes and an optical multiplexer having (i) an input that is configured to receive light from the plurality of superluminescent light-emitting diodes and (ii) a plurality of outputs that are configured to deliver light to the fiber optic radiation delivery system.

6. The sensor system of claim 5 wherein the dispersive element comprises a tunable bandpass filter or a grating spectrometer.

7. The sensor system of claim 5 wherein the detector comprises a detector array and the dispersive element comprises a grating spectrometer or a linear variable filter.

8. The sensor system of claim 1 wherein the high brightness light source comprises a tunable laser diode.

9. The sensor system of claim 8 wherein the detector comprises a single element photodiode.

10. The sensor system of claim 1 wherein the composition comprises paper and the means for analyzing the light from the second fiber optic radiation delivery system calculates the temperature, cellulose content and water content of the paper.

11. The sensor system of claim 1 wherein the fiber optic radiation delivery system comprises one or more first optical fibers that are routed through a first take-up mechanism and the fiber optic radiation retrieval system comprises one or more second optical fibers that are routed through a second take-up mechanism.

12. A method of performing measurements with a sensor that detects a plurality of parameters in a composition that comprises the steps of:
   providing a high brightness light source that is located remotely from the composition;
   providing an optical head comprising a first optics that directs radiation to the composition and a second optics that collects radiation that emerges from the composition;
   providing a fiber optic radiation delivery system for directing radiation from the high brightness light source to the first optics;
   providing a fiber optic radiation retrieval system for receiving radiation that is directed from the second optics and for transmitting the radiation to a radiation detector, wherein the high brightness light source generates illuminating radiation of sufficient optical power density to produce detection radiation along a detection beam path to the radiation detector;
   positioning a dispersive element in the detection beam path; and
   analyzing the light from the fiber optic radiation retrieval system to calculate the plurality of parameters of the composition.

13. The method of claim 12 wherein the high brightness light source comprises a fiber supercontinuum source.

14. The method of claim 13 wherein the dispersive element comprises a tunable bandpass filter or a grating spectrometer.

15. The method of claim 13 wherein the detector comprises a detector array and the dispersive element comprises a grating spectrometer or a linear variable filter.

16. The method of claim 12 wherein the high brightness light source comprises a plurality of superluminescent light-emitting diodes and an optical multiplexer having (i) an input that is configured to receive light from the plurality of superluminescent light-emitting diodes and (ii) a plurality of outputs that are configured to deliver light to the fiber optic radiation delivery system.

17. The method of claim 16 wherein the dispersive element comprises a tunable bandpass filter or a grating spectrometer.

18. The method of claim 16 wherein the detector comprises a detector array and the dispersive element comprises a grating spectrometer or a linear variable filter.

19. The method of claim 12 wherein the high brightness light source comprises a tunable laser diode.

20. The method of claim 19 wherein the detector comprises a single element photodiode.

21. The method of claim 12 wherein the fiber optic radiation delivery system comprises one or more first optical fibers that are routed through a first take-up mechanism and the fiber optic radiation retrieval system comprises one or more second optical fibers that are routed through a second take-up mechanism.

22. The method of claim 21 wherein the fiber optic radiation delivery system and the fiber optic radiation retrieval system are routed through a take-up mechanism along coextensive paths.

23. The method of claim 12 wherein the composition comprises paper and the plurality of parameters include moisture content, temperature, and cellulose content.

* * * * *